United States Patent

Maurer et al.

[11] 4,202,889
[45] May 13, 1980

[54] COMBATING ARTHROPODS WITH O-ALKYL-O-(6-ALKOXY-2-CYCLOPROPYL-PYRIMIDIN-4-YL)-(THIONO)(THIOL)-PHOSPHORIC (PHOSPHONIC) ACID ESTERS OR ESTER-AMIDES

[75] Inventors: Fritz Maurer, Wuppertal; Ingeborg Hammann, Cologne; Wolfgang Behrenz, Overath, all of Fed. Rep. of Germany

[73] Assignee: Bayer Aktiengesellschaft, Leverkusen, Fed. Rep. of Germany

[21] Appl. No.: 931,082

[22] Filed: Aug. 4, 1978

[30] Foreign Application Priority Data

Aug. 19, 1977 [DE] Fed. Rep. of Germany ....... 2737401

[51] Int. Cl.$^2$ ............................ A01N 9/36; C07F 9/65
[52] U.S. Cl. .................................... 424/200; 544/243; 544/319
[58] Field of Search ........................ 544/243; 424/200

[56] References Cited

U.S. PATENT DOCUMENTS

| | | | |
|---|---|---|---|
| 2,754,243 | 7/1956 | Gysin et al. | 424/200 |
| 3,862,188 | 1/1975 | Milzner et al. | 544/243 |
| 4,012,506 | 3/1977 | Balke et al. | 424/200 |

*Primary Examiner*—Alton D. Rollins
*Assistant Examiner*—Diana G. Rivers
*Attorney, Agent, or Firm*—Sprung, Felfe, Horn, Lynch & Kramer

[57] ABSTRACT

O-Alkyl-O-(6-alkoxy-2-cyclopropyl)-pyrimidin-4-yl)-(thiono)(thiol)-phosphoric (phosphonic) acid esters or ester-amides of the formula

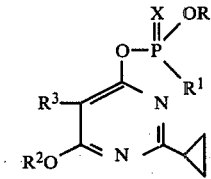

in which
R is alkyl,
$R^1$ is alkyl, alkoxy, alkylthio, monoalkylamino or phenyl,
$R^2$ is alkyl,
$R^3$ is hydrogen, halogen or alkyl, and
X is oxygen or sulphur,
which possess arthropodicidal properties.

10 Claims, No Drawings

COMBATING ARTHROPODS WITH O-ALKYL-O-(6-ALKOXY-2-CYCLOPROPYL-PYRIMIDIN-4-YL)-(THIONO)(THIOL)-PHOSPHORIC (PHOSPHONIC) ACID ESTERS OR ESTER-AMIDES

The present invention relates to and has for its objects the provision of particular new O-alkyl-O-(6-alkoxy-2-cyclopropyl-pyrimidin-4-yl)-(thiono)(thiol)-phosphoric (phosphonic)acid esters or ester-amides which possess arthropodicidal properties, active compositions in the form of mixtures of such compounds with solid and liquid dispersible carrier vehicles, and methods for producing such compounds and for using such compounds in a new way especially for combating pests, e.g. insects and acarids, with other and further objects becoming apparent from a study of the within specification and accompanying examples.

It has already been disclosed that certain O,O-dialkyl-O-pyrimidinylthionophosphoric acid esters, for example O,O-dimethyl-O-[2-ethyl-4-ethoxy-pyrimidin-6-yl]- and O,O-diethyl-O-[2-isopropyl-4-methyl-pyrimidin-6-yl]-thionophosphoric acid ester, have insecticidal and acaricidal properties (see U.S. Pat. Nos. 2,754,243 and 3,862,188).

The present invention now provides, as new compounds, the cyclopropyl-substituted pyrimidin-4-yl(thiono)(thiol)-phosphoric(phosphonic) acid esters and esteramides of the general formula

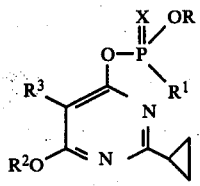

in which
R represents alkyl,
$R^1$ represents alkyl, alkoxy, alkylthio, monoalkylamino or phenyl,
$R^2$ represents alkyl,
$R^3$ represents hydrogen, halogen or alkyl and
X represents oxygen or sulphur.

Preferably, R represents straight-chain or branched alkyl with 1 to 6 (especially 1 to 4) carbon atoms, $R^1$ represents straight-chain or branched alkyl, alkoxy, alkylthio or monoalkylamino, each with 1 to 6 (especially 1 to 4) carbon atoms, or phenyl, $R^2$ represents straight-chain or branched alkyl with 1 to 6 (especially 1 to 4) carbon atoms, $R^3$ represents hydrogen, chlorine, bromine or straight-chain or branched alkyl with 1 to 5 carbon atoms (especially methyl or ethyl) and X represents sulphur.

Surprisingly, the cyclopropyl-substituted pyrimidin-4-yl(thiono)(thiol)-phosphoric(phosphonic) acid esters and ester-amides according to the invention have a better insecticidal and acaricidal action than the known pyrimidin-6-yl-thionophosphoric acid esters of analogous structure and the same type of action. The compounds of the present invention thus represent a true enrichment of the art.

The invention also provides a process for the preparation of a cyclopropyl-substituted pyrimidin-4-yl(thiono)(thiol)-phosphoric(phosphonic) acid ester or ester-amide of the formula (I), in which a (thiono)(thiol)-phosphoric(phosphonic) acid ester halide or ester-amide halide of the general formula

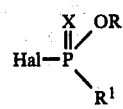

in which
R, $R^1$ and X have the meanings stated above and
Hal represents halogen, preferably chlorine,
is reacted, optionally in the presence of a solvent or diluent, with a 2-cyclopropyl-4-hydroxy-pyrimidine of the general formula

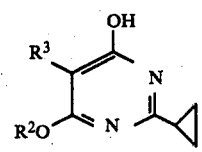

in which $R^2$ and $R^3$ have the meanings stated above, the latter being used as such, in the presence of an acid acceptor, or in the form of an alkali metal salt, alkaline earth metal salt or ammonium salt.

If, for example, O-ethyl-S-n-propyl-thionothiolphosphoric acid diester chloride and 2-cyclopropyl-5-methyl-6-isopropyloxy-4-hydroxy-pyrimidine are used as the starting materials, the course of the reaction can be represented by the following equation:

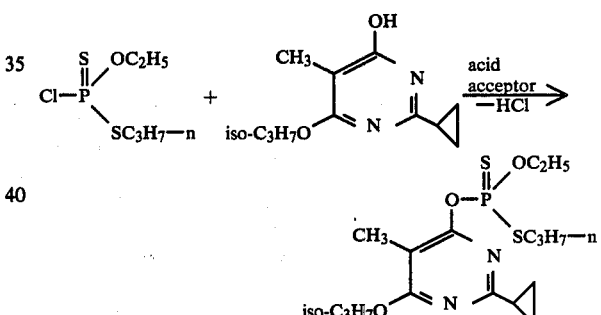

The (thiono)(thiol)-phosphoric(phosphonic) acid ester halides and ester-amide halides (II) to be used as starting materials are known and can be readily prepared, even industrially, by processes which are known from the literature. Examples of these compounds which may be mentioned are: O,O-dimethyl-, O,O-diethyl-, O,O-di-n-propyl-, O,O-di-iso-propyl-, O,O-di-n-butyl-, O,O-di-iso-butyl-, O,O-di-sec.-butyl-, O-methyl-O-ethyl-, O-methyl-O-n-propyl, O-methyl-O-iso-propyl-, O-methyl-O-n-butyl-, O-methyl-O-iso-butyl-, O-methyl-O-sec.-butyl-, O-ethyl-O-n-propyl-, O-ethyl-O-iso-propyl-, O-ethyl-O-n-butyl-, O-ethyl-O-sec.-butyl-, O-ethyl-O-iso-butyl-, O-n-propyl-O-butyl- and O-iso-propyl-O-butyl-phosphoric acid diester chloride and the corresponding thiono analogues; O,S-dimethyl-, O,S-diethyl, O,S-di-n-propyl-, O,S-di-iso-propyl-, O,S-di-n-butyl-, O,S-di-iso-butyl-, O-ethyl-S-n-propyl-, O-ethyl-S-iso-propyl-, O-ethyl-S-n-butyl, O-ethyl-S-sec.-butyl, O-n-propyl-S-ethyl-, O-n-propyl-S-iso-propyl-, O-n-butyl-S-n-propyl- and O-sec.-butyl-S-ethyl-thiolphosphoric acid diester chloride and the corresponding thiono analogues; O-methyl-, O-ethyl-, O-n-propyl-, O-iso-propyl-, O-n-butyl-, O-iso-butyl- and O-sec.-butyl-methane- and -ethane-, -n-propane-, -iso-propane-, -n-butane-, -iso-butane-, -sec.-butane- and -phenyl-phosphonic acid ester chloride and the corresponding thiono analogues; and O-N-dimethyl-, O-methyl-N-ethyl-, O-methyl-N-n-propyl-, O-methyl-N-iso-propyl-, O-ethyl-N-methyl-, O,N-diethyl-, O-ethyl-N-n-propyl-, O-ethyl-N-iso-propyl, O-n-propyl-N-methyl-, O-n-propyl-N-ethyl-, O,N-di-n-propyl-, O-n-propyl-N-iso-propyl-, O-iso-propyl-N-methyl-, O-iso-propyl-N-ethyl-, O-iso-propyl-N-n-propyl-, O,N-di-iso-propyl-, O-n-butyl-N-methyl-, O-n-butyl-N-ethyl-, O-n-butyl-N-n-propyl-, O-n-butyl-N-iso-propyl-, O-iso-butyl-N-methyl-, O-iso-butyl-N-ethyl-, O-iso-butyl-N-n-propyl-, O-iso-butyl-N-iso-propyl-, O-sec.-butyl-N-methyl-, O-sec.-butyl-N-ethyl-, O-sec.-butyl-N-n-propyl- and O-sec.-butyl-N-iso-propyl-phosphoric acid mono-esteramide chloride and the corresponding thiono analogues.

The 2-cyclopropyl-4-hydroxy-pyrimidines (III) which are also to be used as starting materials can be prepared by processes which are known from the literature, by alkylating, for example, 2-cyclopropyl-4,6-dihydroxypyrimidine with, for example, dimethyl sulphate and optionally halogenating the resulting products, for example with bromine.

Examples of the starting materials (III) which may be mentioned are: 6-methoxy-, 6-ethoxy, 6-n-propoxy-, 6-iso-propoxy-, 6-n-butoxy-, 6-sec.-butoxy-, 6-iso-butoxy- and 6-tert.-butoxy-2-cyclopropyl-4-hydroxy-pyrimidine, furthermore 5-chloro-6-methoxy-, 5-chloro-6-ethoxy-, 5-chloro-6-n-propoxy-, 5-chloro-6-iso-propoxy-, 5-chloro-6-n-butoxy-, 5-chloro-6-sec.-butoxy-, 5-chloro-6-iso-butoxy- and 5-chloro-6-tert.-butoxy-2-cyclopropyl-4-hydroxy-pyrimidine; 5-bromo-6-methoxy-, 5-bromo-6-ethoxy-, 5-bromo-6-n-propoxy-, 5-bromo-6-iso-propoxy-, 5-bromo-6-n-butoxy, 5-bromo-6-sec.-butoxy-, 5-bromo-6-iso-butoxy- and 5-bromo-6-tert.-butoxy-2-cyclopropyl-4-hydroxy-pyrimidine; 5-methyl-6-methoxy-, 5-methyl-6-ethoxy-, 5-methyl-6-n-propoxy-, 5-methyl-6-iso-propoxy-, 5-methyl-butoxy-, 5-methyl-6-sec.-butoxy-, 5-methyl-6-iso-butoxy- and 5-methyl-6-tert.-butoxy-2-cyclopropyl-4-hydroxy-pyrimidine; and 5-ethyl-6-methoxy-, 5-ethyl-6-ethoxy-, 5-ethyl-6-n-propoxy-, 5-ethyl-6-iso-propoxy-, 5-ethyl-6-n-butoxy-, 5-ethyl-6-sec.-butoxy-, 5-ethyl-6-iso-butoxy- and 5-ethyl-6-tert.-butoxy-2-cyclopropyl-4-hydroxy-pyrimidine.

The process for the preparation of the compounds according to the invention is preferably carried out also using a suitable solvent or diluent. Possible solvents or diluents are virtually all the inert organic solvents, especially aliphatic and aromatic, optionally chlorinated hydrocarbons, such as benzene, toluene, xylene, benzine, methylene chloride, chloroform, carbon tetrachloride and chlorobenzene; ethers, for example diethyl ether, dibutyl ether and dioxane, ketones, for example acetone, methyl ethyl ketone, methyl isopropyl ketone and methyl isobutyl ketone; and nitriles, such as acetonitrile and propionitrile.

All the customary acid-binding agents can be used as the acid acceptors. Alkali metal carbonates and alcoholates, such as sodium carbonate, methylate and ethylate and potassium carbonate, methylate and ethylate, and aliphatic, aromatic or heterocyclic amines for example triethylamine, trimethylamine, dimethylaniline, dimethylbenzylamine and pyridine, have proved particularly suitable.

The reaction temperature can be varied within a relatively wide range. In general, the reaction is carried out at from 0° to 100° C., preferably at from 20° to 60° C.

In general, the reaction is allowed to proceed under normal pressure.

For carrying out the process, the starting materials are usually employed in stoichiometric amounts. An excess of one or other component brings no substantial advantages. The reactants are usually combined in one of the solvents indicated above, in the presence of an acid acceptor, and the mixture is stirred for one or more hours at elevated temperature in order to bring the reaction to completion. Thereafter, an organic solvent, for example toluene, is added to the mixture and the organic phase is worked up in the customary manner by washing and drying and distilling off the solvent.

The new compounds are frequently obtained in the form of oils, which usually cannot be distilled without decomposition, but can be freed from the last volatile constituents by so-called "incipient distillation," that is to say by prolonged heating to moderately elevated temperatures under reduced pressure, and can be purified in this manner. The refractive index is used for their characterization. Some of the compounds are obtained in the crystalline form and are characterized by their melting point.

As already mentioned, the compounds according to the present invention are distinguished by an excellent insecticidal and acaricidal activity. They are therefore active against plant pests, pests harmful to health and pests of stored products and combine a low phytotoxicity with a good action against sucking and biting insects and against mites.

For this reason, the compounds according to the invention can be employed successfully as pesticides in plant protection and in the hygiene field and the field of protection of stored products.

The compounds according to the present invention can also be used in the field of veterinary medicine.

The active compounds are well tolerated by plants, have a favorable level of toxicity to warm-blooded animals, and can be used for combating arthropod pests, especially insects and acarids, which are encountered in agriculture, in forestry, in the protection of stored products and of materials, and in the hygiene field. They are active against normally sensitive and resistant species and against all or some stages of development. The abovementioned pests include:

from the class of the Isopoda, for example *Oniscus asellus, Armadillidium vulgare* and *Porcellio scaber;* from the class of the Diplopoda, for example *Blaniulus guttulatus;* from the class of the Chilopoda, for example *Geophilus carpophagus* and *Scutigera* spec.;

from the class of the Symphyla, for example *Scutigerella immaculata;* from the order of the Thysanura, for example *Lepisma saccharina;* from the order of the Collembola, for example *Onychiurus armatus;* from the order of the Orthoptera, for example *Blatta orientalis, Periplaneta americana, Leucophaea maderae, Blattella germanica, Acheta domesticus,* Gryllotalpa spp., *Locusta migratoria migratorioides, Melanoplus differentialis* and *Schistocerca gregaria;* from the order of the Dermaptera, for example *Forficula auricularia;* from the order of the Isoptera, for example Reticulitermes spp.;

from the order of the Anoplura, for example *Phylloxera vastatrix*, Pemphigus spp., *Pediculus humanus corporis*, Haematopinus spp. and Linognathus spp.;

from the order of the Mallophaga, for example Trichodectes spp. and Damalinea spp.;

from the order of the Thysanoptera, for example *Hercinothrips femoralis* and *Thrips tabaci;* from the order of the Heteroptera, for example Eurygaster spp., *Dysdercus intermedius, Piesma quadrata, Cimex lectularius, Rhodnius prolixus* and Triatoma spp.;

from the order of the Homoptera, for example *Aleurodes brassicae, Bemisia tabaci, Trialeurodes vaporariorum, Aphis gossypii, Brevicoryne brassicae, Cryptomyzus ribis, Doralis fabae, Doralis pomi, Eriosoma lanigerum, Hyalopterus arundinis, Macrosiphum avenae*, Myzus spp., *Phorodon humuli, Rhopalosiphum padi*, Empoasca spp., *Euscelis bilobatus, Nephotettix cincticeps, Lecanium corni, Saissetia oleae, Laodelphax striatellus, Nilaparvata lugens, Aonidiella aurantii, Aspidiotus hederae*, Pseudococcus spp. and Psylla spp.;

from the order of the Lepidoptera, for example *Pectinophora gossypiella, Bupalus piniarius, Cheimatobia brumata, Lithocolletis blancardella, Hyponomeuta padella, Plutella maculipennis, Malacosoma neustria, Euproctis chrysorrhoea*, Lymantria spp., *Bucculatrix thurberiella, Phyllocnistis citrella*, Agrotis spp., Euxoa spp., Feltia spp., *Earias insulana*, Heliothis spp., *Laphygma exigua, Mamestra brassicae, Panolis flammea, Prodenia litura*, Spodoptera spp., *Trichoplusia ni, Carpocapsa pomonella*, Pieris spp., Chilo spp., *Pyrausta nubilalis, Ephestia kuehniella, Galleria mellonella, Cacoecia podana, Capua reticulana, Choristoneura fumiferana, Clysia ambiguella, Homona magnanima* and *Tortrix viridana;* from the order of the Coleoptera, for example *Anobium punctatum, Rhizopertha dominica, Bruchidius obtectus, Acanthoscelides obtectus, Hylotrupes bajulus, Agelastica alni, Leptinotarsa decemlineata, Phaedon cochleariae*, Diabrotica spp., *Psylliodes chrysocephala, Epilachna varivestis*, Atomaria spp., *Oryzaephilus surinamensis*, Anthonomus spp., Sitophilus spp., *Otiorrhynchus sulcatus, Cosmopolites sordidus, Ceuthorrhynchus assimilis, Hypera postica*, Dermestes spp., Trogoderma spp., Anthrenus spp., Attagenus spp., Lyctus spp., *Meligethes aeneus*, Ptinus spp., *Niptus hololeucus, Gibbium psylloides*, Tribolium spp., *Tenebrio molitor*, Agriotes spp., Conoderus spp., *Melolontha melolontha, Amphimallon solstitialis* and *Costelytra zealandica;* from the order of the Hymenoptera, for example Diprion spp., Hoplocampa spp., Lasius spp., *Monomorium pharaonis* and Vespa spp.;

from the order of the Diptera, for example Aedes spp., Anopheles spp., Culex spp., *Drosophila melanogaster*, Musca spp., Fannia spp., *Calliphora erythrocephala*, Lucilia spp., Chrysomyia spp., Cuterebra spp., Gastrophilus spp., Hyppobosca spp., Stomoxys spp., Oestrus spp., Hypoderma spp., Tabanus spp., Tannia spp., *Bibio hortulanus, Oscinella frit*, Phorbia spp., *Pegomyia hyoscyami, Ceratitis capitata, Dacus oleae* and *Tipula paludosa;* from the order of the Siphonaptera, for example *Xenopsylla cheopis* and Ceratophyllus spp.;

from the class of the Arachnida, for example *Scorpio maurus* and *Latrodectus mactans;* from the order of the Acarina, for example *Acarus siro*, Argas spp., Ornithodoros spp., *Dermanyssus gallinae, Eriophyes ribis, Phyllocoptruta oleivora*, Boophilus spp., Rhipicephalus spp., Amblyomma spp., Hyalomma spp., Ixodes spp., Psoroptes spp., Chorioptes spp., Sarcoptes spp., Tarsonemus spp., *Bryobia praetiosa*, Panonychus spp. and Tetranychus spp.

The active compounds can be converted into the customary formulations, such as solutions, emulsions, wettable powders, suspensions, powders, dusting agents, foams, pastes, soluble powders, granules, aerosols, suspension-emulsion concentrates, seed-treatment powders, natural and synthetic materials impregnated with active compound, very fine capsules in polymeric substances, coating compositions for use on seed, and formulations used with burning equipment, such as fumigating cartridges, fumigating cans and fumigating coils, as well as ULV cold mist and warm mist formulations.

These formulations may be produced in known manner, for example by mixing the active compounds with extenders, that is to say liquid or liquefied gaseous or solid diluents or carriers, optionally with the use of surface-active agents, that is to say emulsifying agents and/or dispersing agents and/or foam-forming agents. In the case of the use of water as an extender, organic solvents can, for example, also be used as auxiliary solvents.

As liquid solvents diluents or carriers, especially solvents, there are suitable in the main, aromatic hydrocarbons, such as xylene, toluene or alkyl naphthalenes, chlorinated aromatic or chlorinated aliphatic hydrocarbons, such as chlorobenzenes, chloroethylenes or methylene chloride, aliphatic or alicyclic hydrocarbons, such as cyclohexane or paraffins, for example mineral oil fractions, alcohols, such as butanol or glycol as well as their ethers and esters, ketones, such as acetone, methyl ethyl ketone, methyl isobutyl ketone or cyclohexanone, or strongly polar solvents, such as dimethylformamide and dimethylsulphoxide, as well as water.

By liquefied gaseous diluents or carriers are meant liquids which would be gaseous at normal temperature and under normal pressure, for example aerosol propellants, such as halogenated hydrocarbons as well as butane, propane, nitrogen and carbon dioxide.

As solid carriers there may be used ground natural minerals, such as kaolins, clays, talc, chalk, quartz, attapulgite, montmorillonite or diatomaceous earth, and ground synthetic minerals, such as highly-dispersed silicic acid, alumina and silicates. As solid carriers for granules there may be used crushed and fractionated natural rocks such as calcite, marble, pumice, sepiolite and dolomite, as well as synthetic granules of inorganic and organic meals, and granules of organic material such as sawdust, coconut shells, corn cobs and tobacco stalks.

As emulsifying and/or foam-forming agents there may be used non-ionic and anionic emulsifiers, such as polyoxyethylene-fatty acid esters, polyoxyethylene-fatty alcohol ethers, for example alkylaryl polyglycol ethers, alkyl sulphonates, alkyl sulphates, aryl sulphonates as well as albumin hydrolysis products. Dispersing agents include, for example, lignin sulphite waste liquors and methylcellulose.

Adhesives such as carboxymethylcellulose and natural and synthetic polymers in the form of powders, granules or latices, such as gum arabic, polyvinyl alcohol and polyvinyl acetate, can be used in the formulations.

It is possible to use colorants such as inorganic pigments, for example iron oxide, titanium oxide and Prussian Blue, and organic dyestuffs, such as alizarin dyestuffs, azo dyestuffs or metal phthalocyanine dyestuffs, and trace nitrients, such as salts of iron, manganese, boron, copper, cobalt, molybdenum and zinc.

The formulations in general contain from 0.1 to 95 percent by weight of active compound, preferably from 0.5 to 90 percent by weight.

The active compounds according to the invention may be used in the form of their formulations of the types that are commercially available or in the use forms prepared from these formulations.

The active compound content of the use forms prepared from the formulations of the types that are commercially available can vary within wide ranges. The active compound concentration of the use forms can be from 0.0000001 to 100% by weight of active compound, preferably from 0.01 to 10% by weight.

The compounds may be employed in a customary manner appropriate for the particular use forms.

When used against pests harmful to health and pests of stored products, the active compounds are distinguished by an excellent residual activity on wood and clay as well as a good stability to alkali on limed substrates.

In the veterinary field, the active compounds according to the invention may be used in a known manner, such as orally in the form of, for example, tablets, capsules, drenches and granules; dermally by means of, for example, dipping, spraying, pouring-on, spotting-on and powdering; and parenterally, for example by means of injections.

The present invention also provides an arthropodicidal composition containing as active ingredient a compound of the present invention in admixture with a solid or liquefied gaseous diluent or carrier or in admixture with a liquid diluent or carrier containing a surface-active agent.

The present invention also provides a method of combating arthropods (especially insects or acarids) which comprises applying to the arthropods, or to a habitat thereof, a compound of the present invention alone or in the form of a composition containing as active ingredient a compound of the present invention in admixture with a diluent or carrier.

The present invention also provides a method of freeing or protecting domesticated animals from ectoparasitical insects or acarids which comprises applying to said animals a compound according to the present invention, in admixture with a diluent or carrier.

The present invention further provides crops protected from damage by arthropods by being grown in areas in which immediately prior to and/or during the time of the growing a compound of the present invention was applied alone or in admixture with a diluent or carrier.

It will be seen that the usual methods of providing a harvested crop may be improved by the present invention.

The present invention further provides domesticated animals whenever freed or protected from ectoparasitical insects or acarids by the application to said animals of a compound according to the present invention, in admixture with a diluent or carrier.

The preparation of the novel compounds is shown in the following illustrative examples wherein the 2-cyclopropyl-4-hydroxy-pyrimidines to be used as starting materials could be prepared, for example, as follows:

EXAMPLE 1

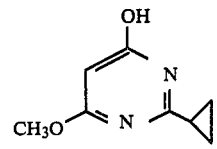
(a)

76 g (0.6 mol) of dimethyl sulphate were added dropwise to a solution of 76 g (0.5 mol) of 2-cyclopropyl-4,6-dihydroxy-pyrimidine in 250 ml of 2 N sodium hydroxide solution at 50° C. The pH value of the reaction solution was kept at 8 to 8.2 by simultaneously adding 2 N sodium hydroxide solution. The mixture was then stirred at 50° C. for a further 2 hours, control of the pH being continued. The mixture was then cooled to 0° C. and the product which had precipitated was filtered off. 33 g (40% of theory) of 2-cyclopropyl-4-hydroxy-6-methoxy-pyrimidine were obtained in this manner in the form of colorless crystals with a melting point of 186° C.

The following compounds of the formula

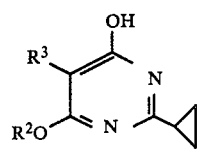
(III)

could be prepared in an analogous manner:

TABLE 1

| Intermediate | $R^2$ | $R^3$ | Yield (% of theory) | Melting point °C. |
|---|---|---|---|---|
| b | $CH_3$ | $CH_3$ | 73 | 199 |
| c | $C_2H_5$ | H | 62 | 158 |
| d | $CH_3$ | Cl | | |
| e | $CH_3$ | $C_2H_5$ | | |
| f | $C_3H_7$-n | H | | |
| g | $C_3H_7$-iso | H | 27 | 150 |
| h | $C_2H_5$ | $C_2H_5$ | | |

EXAMPLE 2

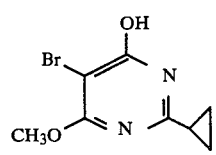
(i)

12 g (0.075 mol) of bromine were added to a solution of 12.4 g (0.075 mol) of 2-cyclopropyl-4-hydroxy-6-methoxypyrimidine in 100 ml of methylene chloride at room temperature. The mixture was subsequently stirred for 1 hour at room temperature and then washed with 100 ml of 2.5% strength sodium bicarbonate solution and with 100 ml of water and the organic phase was dried over sodium sulphate. After distilling off the solvent, 6.7 g (36% of theory) of 2-cyclopropyl-4-hydroxy-5-bromo-6-methoxy-pyrimidine remained as a colorless powder with a melting point of 174° C. (decomposition).

The end products were prepared as follows:

EXAMPLE 3

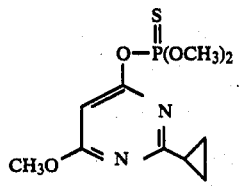

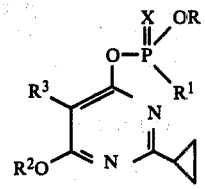

The following compounds of the formula 10 could be prepared analogously:

TABLE 2

| Compound No. | R | $R^1$ | $R^2$ | $R^3$ | X | Yield (% of theory) | Physical data (Refractive index; melting point °C.) |
|---|---|---|---|---|---|---|---|
| 2 | $CH_3$ | $CH_3$ | $CH_3$ | H | S | 78 | $n_D^{23}$:1.5310 |
| 3 | $C_2H_5$ | $OC_2H_5$ | $CH_3$ | H | S | 95 | $n_D^{24}$:1.5166 |
| 4 | $C_2H_5$ | $SC_3H_7$-n | $CH_3$ | H | S | 73 | $n_D^{27}$:1.5449 |
| 5 | $C_2H_5$ | $CH_3$ | $CH_3$ | H | S | 76 | $n_D^{27}$:1.5343 |
| 6 | $C_3H_7$-n | $OC_2H_5$ | $CH_3$ | H | S | 72 | $n_D^{27}$:1.5127 |
| 7 | $C_2H_5$ | $NH-C_3H_7$-iso | $CH_3$ | H | S | 60 | 46 |
| 8 | $C_2H_5$ | $OC_2H_5$ | $CH_3$ | Br | S | 52 | $n_D^{23}$:1.5370 |
| 9 | $C_2H_5$ | $OC_2H_5$ | $CH_3$ | H | O | 83 | $n_D^{24}$:1.4886 |
| 10 | $C_2H_5$ | $OC_2H_5$ | $CH_3$ | $CH_3$ | S | 34 | $n_D^{25}$:1.5170 |
| 11 | $C_2H_5$ | $NH-C_3H_7$-iso | $CH_3$ | H | O | 53 | 44 |
| 12 | $CH_3$ | $NH-CH_3$ | $CH_3$ | H | S | 33 | $n_D^{25}$:1.5402 |
| 13 | $CH_3$ | $OCH_3$ | $C_2H_5$ | H | S | 70 | $n_D^{25}$:1.5254 |
| 14 | $C_2H_5$ | $OC_2H_5$ | $C_2H_5$ | H | S | 81 | $n_D^{25}$:1.5130 |
| 15 | $C_2H_5$ | $OC_2H_5$ | $CH_3$ | Cl | S | | |
| 16 | $C_2H_5$ | phenyl | $CH_3$ | H | S | 68 | $n_D^{22}$: 1.5783 |
| 17 | $C_3H_7$-iso | $CH_3$ | $CH_3$ | H | S | 70 | $n_D^{23}$: 1.5281 |
| 18 | $C_2H_5$ | $C_2H_5$ | $CH_3$ | H | S | 72 | $n_D^{22}$: 1.5402 |
| 19 | $C_2H_5$ | $OC_2H_5$ | $CH_3$ | $C_2H_5$ | S | | |
| 20 | $C_2H_5$ | $OC_2H_5$ | $C_2H_5$ | $C_2H_5$ | S | | |
| 21 | $C_2H_5$ | $OC_2H_5$ | $C_3H_7$-n | H | S | | |
| 22 | $C_2H_5$ | $OC_2H_5$ | $C_3H_7$-iso | H | S | 66 | $n_D^{24}$: 1.5110 |
| 23 | $CH_3$ | $OCH_3$ | $C_3H_7$-iso | H | S | | |
| 24 | $C_2H_5$ | $SC_3H_7$-n | $CH_3$ | H | O | 57 | $n_D^{23}$:1.5247 |
| 25 | $C_2H_5$ | $SC_3H_7$-n | $C_2H_5$ | H | S | 71 | $n_D^{25}$:1.5418 |
| 26 | $C_2H_5$ | $SC_3H_7$-n | $C_2H_5$ | H | O | | |
| 27 | $C_2H_5$ | $C_2H_5$ | $C_2H_5$ | H | S | 80 | $n_D^{22}$: 1.5328 |
| 28 | $C_2H_5$ | $CH_3$ | $C_2H_5$ | H | S | 77 | $n_D^{22}$: 1.5305 |
| 29 | $C_3H_7$-iso | $CH_3$ | $C_2H_5$ | H | S | 62 | 54 |
| 30 | $C_2H_5$ | phenyl | $C_2H_5$ | H | S | 72 | $n_D^{25}$: 1.5677 |
| 31 | $C_3H_7$-n | $C_2H_5$ | $CH_3$ | H | S | 69 | $n_D^{23}$ : 1.5262 |
| 32 | $C_2H_5$ | $CH_3$ | $C_3H_7$-iso | H | S | 77 | $n_D^{21}$ : 1.5232 |
| 33 | $C_2H_5$ | $C_2H_5$ | $C_3H_7$-iso | H | S | 81 | $n_D^{21}$ : 1.525 |

A mixture of 16.6 g (0.1 mol) of 2-cyclopropyl-4-hydroxy-6-methoxy-pyrimidine, 20.7 g (0.15 mol) of potassium carbonate, 16 g (0.1 mol) of O,O-dimethylthionophosphoric acid diester chloride and 300 ml of acetonitrile was stirred at 50° C. for 4 hours. The mixture was cooled to room temperature and, after adding 400 ml of toluene, was extracted by shaking twice with 300 ml of water each time. The organic phase was separated off, dried over sodium sulphate and freed from the solvent in vacuo and the residue was subjected to incipient distillation. 22.6 g (78% of theory) of O,O-dimethyl-O-(2-cyclopropyl-6-methoxy-pyrimidin-4-yl)-thiono-phosphoric acid ester were thus obtained in the form of a yellow oil having a refractive index $n_D^{23}$ of 1.5441.

The following compounds of the formula

The insecticidal and acaricidal activity of the compounds of this invention is illustrated by the following examples:

EXAMPLE 4

Phaedon larvae test

Solvent: 3 parts by weight of acetone
Emulsifier: 1 part by weight of alkylaryl polyglycol ether To produce a suitable preparation of active compound, 1 part by weight of the active compound was mixed with the stated amount of solvent containing the stated amount of emulsifier and the concentrate was diluted with water to the desired concentration.

Cabbage leaves (*Brassica oleracea*) were sprayed with the preparation of the active compound until dripping wet and were then infested with mustard beetle larvae (*Phaedon cochleariae*).

After certain times, the destruction in % was determined. In this test, for example, Compounds 1, 3, 6, 9 and 14 showed an excellent action which was distinctly superior to the action of compounds known from the state of the art.

EXAMPLE 5

Tetranychus test (resistant)

Solvent: 3 parts by weight of acetone
Emulsifier: 1 part by weight of alkylaryl polyglycol ether To produce a suitable preparation of active compound, 1 part by weight of the active compound was mixed with the stated amount of solvent and the stated amount of emulsifier and the concentrate was diluted with water to the desired concentration.

Bean plants (*Phaseolus vulgaris*) which were heavily infested with the two-spotted spider mite (*Tetranychus urticae*) in all stages of development were sprayed with the preparation of the active compound until dripping wet.

After certain times, the destruction in % was determined. In this test, for example, Compounds 2, 3, 4 and 5 showed an excellent action which was distinctly superior to the action of compounds known from the state of the art.

EXAMPLE 6

LD$_{100}$ test

Test insects: *Sitophilus granarius*
Solvent: Acetone

The active compound was taken up in the solvent at a rate of 2 g per liter. The solution so obtained was diluted with further solvent to the desired concentrations.

2.5 ml of the solution of the active compound were pipetted into a Petri dish. On the bottom of the Petri dish there was a filter paper with a diameter of about 9.5 cm. The Petri dish remained uncovered until the solvent had completely evaporated. The amount of active compound per square meter of filter paper varied with the concentration of the solution of active compound. About 25 test insects were then placed in the Petri dish and it was covered with a glass lid.

The condition of the test insects was observed 3 days after the commencement of the experiments. The destruction, in %, was determined.

In this test, for example, Compounds 1, 2, 3 and 4 showed an excellent action which was distinctly superior to the action of compounds known from the state of the art.

EXAMPLE 7

Test with parasitic fly larvae

Emulsifier: 80 parts by weight of Cremophor EL

To produce a suitable preparation of active compound, 20 parts by weight of the active compound in question were mixed with the stated amount of the emulsifier and the mixture thus obtained was diluted with water to the desired concentration.

About 20 fly larvae (*Lucilia cuprina*, res.) were introduced into a test tube which contained about 3 ml of a 20% strength suspension of egg yolk powder in water, and which was fitted with a cottonwool plug of appropriate size. 0.5 ml of the active compound preparation was placed on this egg yolk powder suspension. After 24 hours, the degree of destruction in % was determined.

In this test, for example, Compounds 1 to 7, 9 and 11 showed an excellent action.

EXAMPLE 8

Test with parasitic adult cattle ticks (*Boophilus microplus* res.)

Solvent: Cremophor

To produce a suitable preparation of active compound, the active substance in question was mixed with the stated solvent in the ratio of 1:2 and the concentrate thus obtained was diluted with water to the desired concentration.

10 Adult cattle ticks (*B. microplus* res.) were dipped for 1 minute into the active compound preparation to be tested. After transfer of the ticks into plastic beakers and storage in a climatically controlled room, the degree of destruction in percent was determined.

In this test, for example, Compound 4 showed an excellent action.

It will be appreciated that the instant specification and examples are set forth by way of illustration and not limitation, and that various modifications and changes may be made without departing from the spirit and scope of the present invention.

What we claim is:

1. An O-alkyl-O-(6-alkoxy-2-cyclopropyl-pyrimidin-4-yl)-(thiono)(thiol)-phosphoric (phosphonic) acid ester or ester-amide of the formula

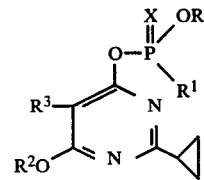

in which
R is alkyl with 1 to 6 carbon atoms,
R$^1$ is alkyl, alkoxy, alkylthio or monoalkylamino each with 1 to 6 carbon atoms, or phenyl,
R$^2$ is alkyl with 1 to 6 carbon atoms,
R$^3$ is hydrogen, halogen or alkyl with 1 to 5 carbon atoms, and
X is oxygen or sulphur.

2. A compound according to claim 1, in which
R$^3$ is hydrogen, chlorine, bromine, or alkyl with 1 to 5 carbon atoms, and
X is sulphur.

3. A compound according to claim 1, wherein such compound is O,O-dimethyl-O-(2-cyclopropyl-6-methoxy-pyrimidin-4-yl)-thionophosphoric acid ester of the formula

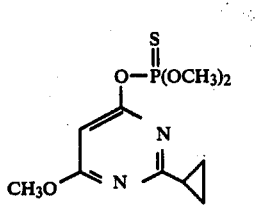

4. A compound according to claim 1, wherein such compound is O-methyl-O-(2-cyclopropyl-6-methoxy-pyrimidin-4-yl)-methanethionophosphonic acid ester of the formula

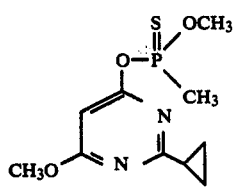

5. A compound according to claim 1, wherein such compound is O-ethyl-O-(2-cyclopropyl-6-methoxy-pyrimidin-4-yl)-methanethionophosphonic acid ester of the formula

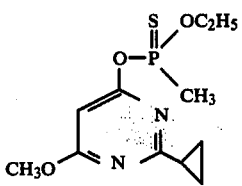

6. A compound according to claim 1, wherein such compound is O,O-diethyl-O-(2-cyclopropyl-6-methoxy-pyrimidin-4-yl)-phosphoric acid ester.

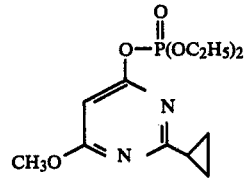

7. A compound according to claim 1, wherein such compound is O,O-diethyl-O-(2-cyclopropyl-6-ethoxy-pyrimidin-4-yl)-thionophosphoric acid ester of the formula

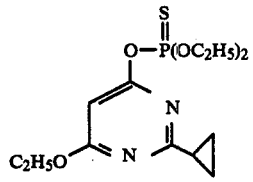

8. An arthropodicidal composition containing as active ingredient an arthropodicidally effective amount of a compound according to claim 1 in admixture with a diluent.

9. A method of combating arthropods which comprises applying to the arthropods, or to a habitat thereof, an arthropodicidally effective amount of a compound according to claim 1.

10. The method according to claim 9 in which said compound is applied to domesticated animals to free them from ectoparasitical insects and acarids, said compound being
O,O-dimethyl-O-(2-cyclopropyl-6-methoxy-pyrimidin-4-yl)-thionophosphoric acid ester,
O-methyl-O-(2-cyclopropyl-6-methoxy-pyrimidin-4-yl)-methanethionophosphonic acid ester,
O-ethyl-O-(2-cyclopropyl-6-methoxy-pyrimidin-4-yl)-methanethionophosphonic acid ester,
O,O-diethyl-O-(2-cyclopropyl-6-methoxy-pyrimidin-4-yl)-phosphoric acid ester, or
O,O-diethyl-O-(2-cyclopropyl-6-ethoxy-pyrimidin-4-yl)-thionophosphoric acid ester.

* * * * *

UNITED STATES PATENT AND TRADEMARK OFFICE
CERTIFICATE OF CORRECTION

PATENT NO. : 4,202,889
DATED : May 13, 1980
INVENTOR(S) : Fritz Maurer et al

It is certified that error appears in the above-identified patent and that said Letters Patent are hereby corrected as shown below:

Please add the name of the fourth inventor "Wilhelm Stendel".

Signed and Sealed this

Twenty-third Day of September 198

[SEAL]

Attest:

SIDNEY A. DIAMOND

Attesting Officer

Commissioner of Patents and Trademark